US006767654B2

(12) United States Patent
Tamao et al.

(10) Patent No.: US 6,767,654 B2
(45) Date of Patent: *Jul. 27, 2004

(54) ORGANIC ELECTROLUMINESCENT DEVICE

(75) Inventors: Kouhei Tamao, Kyoto (JP); Shigehiro Yamaguchi, Uji (JP); Manabu Uchida, Yokohama (JP); Takaharu Nakano, Yokosuka (JP); Toshihiro Koike, Yokohama (JP); Takenori Izumizawa, Yokohama (JP); Kenji Furukawa, Yokosuka (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/869,920

(22) PCT Filed: Dec. 22, 1999

(86) PCT No.: PCT/JP99/07219

§ 371 (c)(1),
(2), (4) Date: Aug. 24, 2001

(87) PCT Pub. No.: WO00/40586

PCT Pub. Date: Jul. 13, 2000

(65) Prior Publication Data

US 2003/0152800 A1 Aug. 14, 2003

(30) Foreign Application Priority Data

Jan. 8, 1999 (JP) ................................................ 11-2786

(51) Int. Cl.[7] .......................... B32B 19/00; B32B 9/00; H01J 1/62; H01J 63/04; C07F 5/02; C07F 9/02
(52) U.S. Cl. ........................ 428/690; 428/917; 313/503; 313/504; 252/40; 568/1; 568/3; 568/6
(58) Field of Search ..................... 568/1, 3, 6; 428/690, 428/917; 313/503, 504; 252/40; 528/394

(56) References Cited

U.S. PATENT DOCUMENTS 5,807,905 A * 9/1998 Cunningham et al. ......... 522/25
6,087,062 A * 7/2000 Cunningham et al. ... 430/270.1

FOREIGN PATENT DOCUMENTS

DE      25 34 713    2/1977
EP      0 775 706    5/1997
WO      98/36035     8/1998

OTHER PUBLICATIONS

CA:73:72398 abs of int. J Appl. Radiat Isotp by Casas et al 21(7) pp 415–20 1970.*
CA:127:67402 abs o f EP775706 May 1997.*
CA:127:88071 abs of DE 19648256 May 1997.*
CA:133:135342 abs of Journal of the American Chemical Society by Yamaguchi et al 122(26) pp6335–6336 2000.*
CA:69:47731 abs of Uch Zap. Perm Gos Univ by Kapkin et al NO 159 pp264–9 1966.*
CA:80:14431 abs of J Amer, Chem Soc by Blount et al 95(21) pp 7019–29 1973.*
Corriu, R., et al. "Unsaturated polymers containing boron and thiopene units in the backbone". J. Chem. Soc. Chem. Commun., (1998), pp. 963–964.
Matsumi, N., et al. "Poly(p–phenylene–borane)s. Novel Organoboron π–Conjugated Polymers via Grignard Reagent", J. Am. Chem. Soc., vol. 120 (1998), pp. 10776–10777.
Matsumi, N., et al. "Extension of π–Conjugation Length via the Vacant p–Orbital of the Boron Atom. Synthesis of Novel Electron Deficient π–Conjugated Systems by Hydroboration Polymerization and Their Blue Light Emission", J. Am. Chem. Soc., vol. 120 (1998), pp. 5112–5113.

(List continued on next page.)

Primary Examiner—Cynthia H. Kelly
Assistant Examiner—Camie S Thompson
(74) Attorney, Agent, or Firm—Wenderoth, Lind & Ponack, L.L.P.

(57) ABSTRACT

This invention relates to a borane derivative represented by the formula (1) and an organic electroluminescent device:

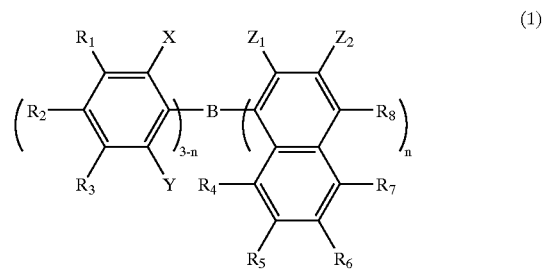

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3; with the provisos that when n is two or more, $Z_1$s may be different from each other; and that cases where n is 1, X, Y and $R_2$ are each methyl, and $R_8$ is hydrogen or substituted boryl and those where n is 3 and $Z_1$ is methyl are excluded. The borane derivatives of this invention are suitable for luminescent materials by virtue of their high luminous efficiencies in solid states, and useful for electrophotography and as photoelectronic functional materials including nonlinear optical materials and conductive materials. The use of this borane derivative brings about an organic EL device characterized by low electricity consumption and high efficiency.

11 Claims, No Drawings

OTHER PUBLICATIONS

Yuan, Z., et al. "Third–order Nonlinear Optical Properties of Organoboron Compounds: Molecular Structures and Second Hyperpolarizabilities", Applied Organometallic Chemistry, vol. 10 (1986), pp. 305–316.

Noda, T., et al. "5,5'–Bis(dimesitylboryl)–2,2'–bithiophene and 5,5"–Bis(dimesitylboryl)–2,2':5',2"–terthiophene as a Novel Family of Electron–Transporting Amorphous Molecular Materials", J. Am. Chem. Soc., vol. 120 (1998), pp. 9714–9715.

"Optical Function Materials", Functional Polymer Material Series, Society of Polymer Science, Japan ed., Kyoritsu Shuppan Co., Ltd. (1991), p. 236.

$40^{th}$ Japan Applied Physics Related Association Lecture Proc., (1993), p. 1146.

Tanaka, H., et al. "Novel hole–transporting materials based on triphenylamine for organic electroluminescent devices", J. Chem. Soc. Chem. Commun., (1996), pp. 2175–2176.

Kuwabara, Y., et al. "Thermally Stable Multilayered Organic Electroluminescent Devices Using Novel Starburst Molecules, 4,4',4"–Tri(N–carbazolyl)triphenylamine (TCTA) and 4,4',4"–Tris(3–methylphenylphenyl–amino)triphenylamine (m–MTDATA), as Hole–Transport Materials", Advance Material, vol. 6 (1994), pp. 677–679.

Yamaguchi, Y., et al. "Application of Unsymmetrical Diphenoquinone Derivatives to Xerography (I)—Molecular Design of a Novel Class of Polymer–dispersible Electron–transport–active Compounds", Journal of the Society of Electrophotography of Japan, vol. 30 (1991), pp. 2–9.

Adachi, C., et al. "Electrolunimescence in Organic Films with Three–Layer Structure", Japanese Journal of Applied Physics, vol. 27, No. 2 (1998), pp. L269–L271.

Adachi, C., et al. "Organic Electroluminescent Device with a Three–Layer Structure", Japanese Journal of Applied Physics, vol. 27, No. 4 (1988), pp. L713–L715.

Adachi, C., et al. "Organic electroluminescent device having a hole conductor as an emitting layer", Appl. Phys. Lett., vol. 55, No. 15 (1989), pp. 1489–1491.

Kido, J., et al. "1,2,3–Triazole Derivative as an Electron Transport Layer in Organic Electroluminescent Devices", Jpn. J. Appl. Physics, vol 32 (1993), pp. L916–L920.

Kido, J., et al. "Organic electroluminescent devices using 1,3,4–thiadiazole derivatives", Polymer Reprints, Japan, vol. 43, No. 3 (1994), p. 987.

Izumizawa, T., et al. "Study on Electroluminescent Behaviors of Metal (III)–quinolinolates", Technical Report of Institute of Electronics, Information and Communication Engineers, vol. 92, No. 311 (1992), pp. 43–48.

Yamamoto, T., et al. "Polymer Light–Emitting Diodes with Single– and Double–Layer Structures Using Poly(2,3–diphenylquinoxaline–5,8–diyl)", Jpn. J. Appl. Phys., vol. 33 (1994), pp. L250–L253.

Nakada, H., et al. "Blue Organic Electroluminescent Devices using Phenanthrolin Derivatives as an Electron Transport Layer", Polymer Reprints, Japan, vol. 43, No. 7 (1994), p. 2450–2451,14J07.

$72^{nd}$ CSJ National Meeting, Lecture Proc. (II), p. 1392, 2PB098, published Mar. 12, 1997.

Abstract of JP 07–102251 Apr. 1995.
Abstract of JP 63–264692 Nov. 1988.
Abstract of JP 7–278537 Oct. 1995.
Abstract of JP 04–363891 Dec. 1992.
Abstract of JP 57–144558 Sep. 1982.
Abstract of JP 61–062038 Mar. 1986.
Abstract of JP 61–124949 Jun. 1986.
Abstract of JP 61–134354 Jun. 1986.
Abstract of JP 61–134355 May 1987.
Abstract of JP 61–112164 May 1986.
Abstract of JP 04–308688 Oct. 1992.
Abstract of JP 06–312979 Nov. 1994.
Abstract of JP 06–267658 Sep. 1994.
Abstract of JP 07–090256 Apr. 1995.
Abstract of JP 07–097355 Apr. 1995.
Abstract of JP 06–001972 Jan. 1994.
Abstract of JP 07–126226 May 1995.
Abstract of JP 07–126615 May 1995.
Abstract of JP 07–331238 Dec. 1995.
Abstract of JP 08–100172 Apr. 1996.
Abstract of JP 08–048656 Feb. 1996.
Abstract of JP 04–212286 Aug. 1992.

John F. Blount et al., "Conformational Analysis of Triarylboranes", Journal of the American Chemical Society, vol. 95, No. 21, 7019–7029, 1973.

* cited by examiner

ORGANIC ELECTROLUMINESCENT DEVICE

This application is a 371 application of PCT/JP99/07219 filed Dec. 22, 1999.

TECHNICAL FIELD

The present invention relates to novel borane derivatives, various materials and organic electroluminescent devices (hereinafter referred to as "organic EL device") comprising the borane derivatives. Specifically, this invention relates to borane derivatives having novel structures, and various materials and organic EL devices comprising the borane derivatives having the structures, which are useful as electronic functional materials and optical functional materials.

BACKGROUND ART

Various institutions have tried to apply π electron type organic compounds to optical functional materials and electronic functional materials in various ways.

Among them, borane compounds which intramolecularly contain boron atoms have unique optic and electronic properties probably owing to the existence of the empty p orbital of the boron atom. However, the borane compounds have generally been unsuitable for the use as such materials, because of their instability to air and water.

With respect to such a problem, it has been reported that the borane compound can become stable to air and water when constituted so as to be bulky, namely, when introducing bulky substituents around a boron atom so as not to expose the boron atom outward. Thus it is highly likely that the borane compound having such a structure can apply for nonlinear optical materials and organic EL devices.

Examples of borane compounds stable in the air have been reported in J. Chem. Soc. Chem. Commun., 1998, 963 (hereinafter referred to as Document 1), J. Am. Chem. Soc., 120, 10776(1998) (hereinafter referred to as Document 2), and J. Am. Chem. Soc., 120, 5112 (1998) hereinafter referred to as Document 3). Further, applications of borane compounds to nonlinear optical materials have been reported in Appl. Organomet. Chem., 10, 305(1996) (hereinafter referred to as Document 4). In addition, an application of borane compounds to organic EL devices has been reported in J. Am. Chem. Soc., 120, 9714 (1998) (hereinafter referred to as Document 5).

Documents 2 and 3 describe the maximum fluorescent wavelength, but the descriptions are limited to the luminescence property in solution state. There is no description on the luminescence property in solid state which is actually used in such application. Further, the structures disclosed are limited to polymers, and there is no description on any low molecular weight compounds.

Document 4 also describes the fluorescent property in the solution state, but there is neither description about the luminescence in the solid state, nor description about applications for the luminescent materials.

Thus the studies have not been made sufficiently for using the "bulky" borane compound in any substantial applications at present. Particularly, there has been a demand to apply the borane material to the organic EL devices. Many studies have been made in order to find such a compound as the device, which has not led to any satisfactory result yet.

The organic EL device essentially comprises a structure wherein an organic compound as a charge transport material and/or a luminescent material is sandwiched in between two electrodes. The highly efficient organic EL device of a low power consumption is required, and thus it is necessary to select an organic compound of high luminous efficiency as the luminescent material.

Document 5 describes some borane compounds such as 5,5'-bis(dimesitylboryl)-2,2'-(bithiophene) and 5,5"-bis(dimesitylboryl)-2,2':5',2"-(terthiophene) used for electron transport materials (charge transport materials), but does not mention their luminescence property or suitability for luminescent materials. This literature merely mentions the device comprising the borane compound having a lower current density, i.e., a more improved luminous efficiency, than that of the device of the same luminance not comprising the borane compound.

JP-A 7-102251 also describes an example of the boron compound used for the organic EL device. However, this boron compound requires a high voltage for driving the device, and has a low luminance.

Since there are few literatures on the luminescence property of borane compounds, any highly efficient organic EL device of a low power consumption has not been prepared by using borane compounds known as a raw material for the organic EL device. Therefore, there has been a demand for a borane compound having a specific structure effective as a material for an organic EL device.

DISCLOSURE OF THE INVENTION

The present inventors have made intensive studies in order to provide a new borane derivative, and various materials and organic EL devices each comprising the borane derivative. As a result, the inventors have found that a borane derivative having a specific structure, and a material, particularly an organic EL device, comprising the borane derivative can solve the above-mentioned problems, whereby the present invention have been achieved.

The present invention is described below in detail.

The borane derivative of the present invention is a new compound represented by the following formula (1). The present borane derivative is expected to be used in a wide variety of applications such as electronic functional materials and optical function materials taking advantage of electronic properties originating from the borane atom, as well as for luminescent materials and charge transport materials.

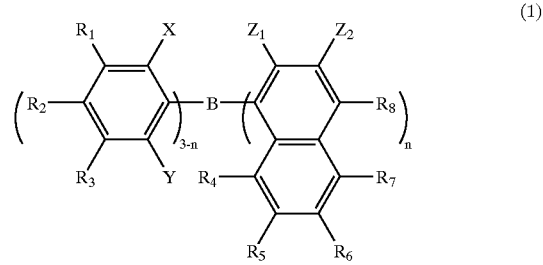

(1)

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3;

with the provisos that when n is two or more, $Z_1$s may be different from each other; and that cases where n is 1, X, Y and $R_2$ are each methyl, and $R_8$ is a hydrogen atom or substituted boryl and those where n is 3 and $Z_1$ is methyl are excluded.

Among the borane derivatives represented by the formula (1), preferable are those wherein at least one substituted or unsubstituted 9-anthryl group is bonded to the boron atom.

Concrete examples of the borane derivative according to this invention include the compounds represented by the following formulae (3) to (9).

(3)

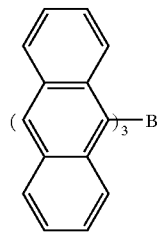

The compound represented by the formula (3) is one of the borane derivatives of the above formula (1) wherein n is 3, $R_4$ to $R_8$ are each hydrogen atom, and $Z_1$ and $Z_2$ are benzo-condensed.

(4)

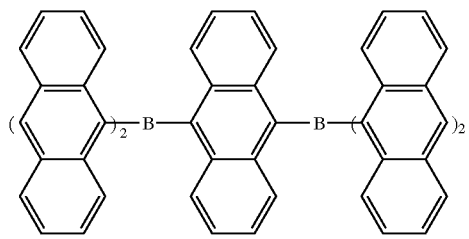

The compound represented by the formula (4) is one of the borane derivatives of the above formula (1) wherein n is 3, $R_4$ to $R_7$ are each hydrogen atom, one $R_8$ is a dianthrylboryl group and the other two $R_8$s are each hydrogen atom, and $Z_1$ and $Z_2$ are benzo-condensed.

(5)

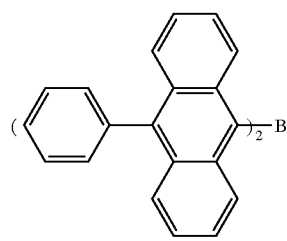

The compound represented by the formula (5) is one of the borane derivatives of the above formula (1) wherein $R_4$ to $R_7$ are each hydrogen atom, $R_8$ is phenyl, n is 3, and $Z_1$ and $Z_2$ are benzo-condensed.

(6)

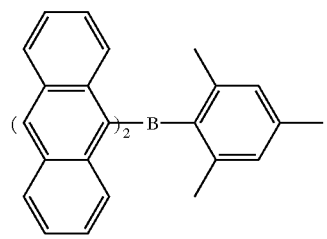

The compound represented by the formula (6) is one of the borane derivatives of the above formula (1) wherein n is 2, $R_1$ and $R_3$ to $R_8$ are each hydrogen atom, $R_2$, X and Y are each methyl group, and $Z_1$ and $Z_2$ are benzo-condensed.

(7)

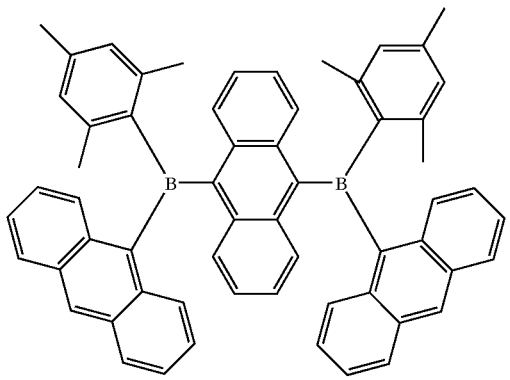

The compound represented by the formula (7) is one of the borane derivatives of the above formula (1) wherein n is 2, $R_1$ and $R_3$ to $R_7$ are each hydrogen atom, $R_2$, X and Y are each methyl group, one $R_8$ is anthrylmesitylboryl, the other $R_8$ is a hydrogen atom, and $Z_1$ and $Z_2$ are benzo-condensed.

(8)

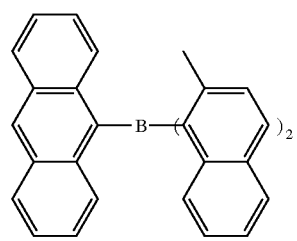

The compound represented by the formula (8) is one of the borane derivatives of the above formula (1) wherein n is 3, $R_4$ to $R_8$ are each hydrogen atom, $Z_1$ and $Z_2$ are benzo-condensed at one position, the other two $Z_1$s not condensed are a methyl group, and the other two $Z_2$s not condensed are a hydrogen atom.

(9)

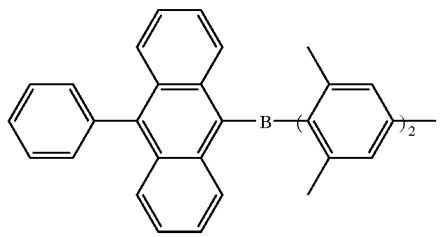

The compound represented by the formula (9) is one of the borane derivatives of the above formula (1) wherein n is 1, $R_1$ and $R_3$ to $R_7$ are each hydrogen atom, $R_2$, X and Y are each methyl group, $R_8$ is a phenyl group, and $Z_1$ and $Z_2$ are benzo-condensed.

The borane derivative, which is used as various materials according to this invention, namely, luminescent materials, charge transport materials and materials for organic EL devices (luminescent layer, charge transport layer), is represented by the following formula (2):

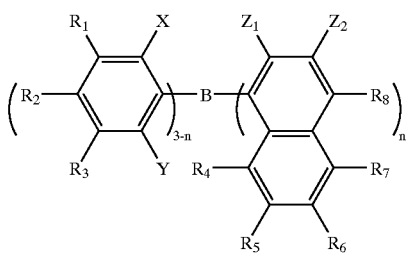

(2)

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3; with the proviso that when n is two or more, $Z_1$s may be different from each other.

The borane derivative preferably has a "bulky" structure so as to be stable even in the air and to show enough durability and performance as such a material. The borane derivative preferably has an anthracene ring and/or a naphthalene ring.

Therefore, the luminescent material, charge transport material and organic EL device of this invention preferably comprise the borane derivatives represented by the formula (2), wherein at least one substituted or unsubstituted 9-anthryl group is bonded to a boron atom.

Concrete examples of such a borane derivative include the compounds represented by the following formulae (10) to (14), in addition to those of the aforementioned formulae (3) to (9).

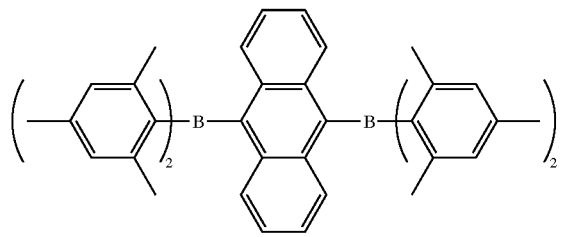

(10)

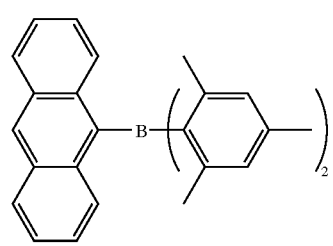

(11)

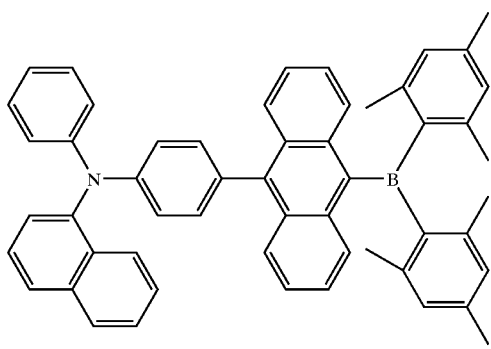

(12)

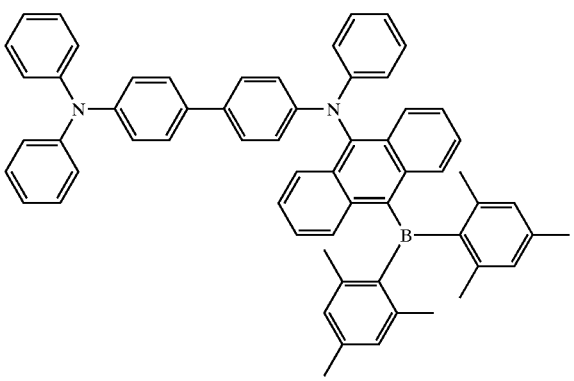

(14)

The borane derivative according to this invention and the borane derivative used for the materials according to this invention (hereinafter abbreviated as "the borane derivative of this invention" for convenience) may be synthesized by various known methods including a typical synthesis shown below. Specifically, the borane derivative of this invention can be obtained by the reaction of the compound represented by the following formula (15) with a base, followed by the reaction with a borane compound.

ArW (15)

wherein Ar denotes the following formula (16) or (17), and W is a halogen atom.

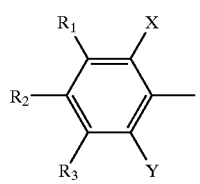
(16)

wherein $R_1$ to $R_3$ are each independently a hydrogen atom, a saturated or unsaturated hydrocarbon group, an aromatic group, a heterocyclic group, a substituted amino group, a substituted boryl group, an alkoxy group or an aryloxy group; and X and Y are each independently a saturated or unsaturated hydrocarbon group, an aromatic group, a heterocyclic group, a substituted amino group, an alkoxy group or an aryloxy group; and

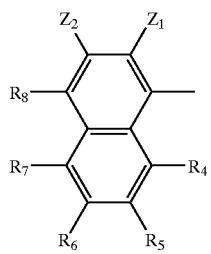
(17)

wherein $R_4$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; and $Z_1$ is a saturated or unsaturated hydrocarbon group, an aromatic group, a heterocyclic group, a substituted amino group, an alkoxy group or an aryloxy group; or $Z_1$ and $Z_2$ may be united to form a condensed ring.

The base to be used in this method includes, for example, organolithium reagents such as n-butyl lithium, tert-butyl lithium and phenyl lithium, and magnesium reagents such as magnesium and magnesium bromide. The solvent to be used is not particularly limited and any solvent may be used as far as it is inert to the base used. In general, ether solvents such as diethyl ether and tetrahydrofuran (hereinafter abbreviated as "THF"), and aromatic solvents such as benzene and toluene may be used. The borane compound to be used includes halogenated boranes such as trichloro borane, trifluoro borane, and complexes thereof; and alkoxy boranes such as trimethoxy borane and triisopropoxy borane.

The reactions as mentioned above are preferably carried out in an inert gas such as nitrogen and argon gas. The reaction temperature is not particularly limited but usually and preferably in the range of −78° C. to 120° C. The reaction time is not particularly limited also, and the reaction may be stopped when the reaction sufficiently progressed. The reaction may be confirmed by a conventional analytical means such as NMR and chromatography, and the end of the reaction may be determined at the optimum point in the analysis.

The borane derivatives of this invention may also be obtained by substitution reaction of the compound obtained by above-mentioned method. The substituent to be added to the compound by the substitution may include alkyl groups such as methyl, ethyl, n-propyl, isopropyl, cyclopentyl and tert-butyl; alkenyl groups such as vinyl, allyl, butenyl and styryl; alkoxy or aryloxy groups such as methoxy, ethoxy, propoxy and phenyloxy; amino groups such as dimethylamino and diphenylamino; silyl groups such as trimethylsilyl, dimethyl-tert-butyl silyl, trimethoxysilyl and triphenylsilyl; boryl groups such as dianthrylboryl and dimesitylboryl; aryl groups such as phenyl, naphthyl, anthryl, biphenyl, toluyl, pyrenyl, perylenyl, anisyl, terphenyl and phenanthrenyl; and heterocyclic groups such as hydrofuryl, hydropyrenyl, dioxanyl, thienyl, furyl, oxazolyl, oxadiazolyl, thiazolyl, thiadiazolyl, acridinyl, quinolyl, quinoxalinyl, phenanthrolinyl, benzothienyl, benzothiazolyl, indolyl, silacyclopentadienyl and pyridyl.

In addition, these substituents may form a ring structure by bonding to each other at any site in the compound.

The organic EL device according to this invention essentially has a structure wherein a borane derivative layer comprising the borane derivative represented by the formula (2) as a main component is sandwiched in between a pair of electrodes (anode and cathode).

The borane derivative is suitable as a material for both a luminescent layer and a charge transport layer (hole injection layer, hole transport layer, electron injection layer and electron transport layer), because it can be used as both a luminescent material and an electron injection material. The borane derivative layer thus obtained effectively acts as a luminescent layer and a charge transport layer.

The borane derivative layer may further comprise any of hole injection materials, hole transport materials, luminescent materials, electron injection materials and electron transport materials in addition to the borone derivative of this invention.

The organic EL device may comprise an electron-donating compound and an electron-accepting compound, which are added in admixture or laminated, as a charge transport material in many cases. It is known that these compounds form unfavorable charge-transfer complex or exciplex. However, the borane derivatives of this invention has a structure in which "bulky" substituents bonded to a boron atom are propeller-like located around the boron atom, and therefore, it is difficult to form the charge-transfer complex or exciplex in this compound. Accordingly, the highly efficient element can advantageously be obtained, when using borane derivatives for the organic EL device as the electron-donating compound or electron-accepting compound.

The organic EL device according to this invention may optionally comprise any additional layers such as hole injection layers, hole transport layers, luminescent layers, electron injection layers, electron transport layers and interlayers, in addition to the borane derivative layer, between the electrodes.

The following are concrete examples of the organic EL device of this invention having laminated structures:

(1) anode/borane derivative layer/cathode;
(2) anode/hole injection layer/borane derivative layer/cathode;
(3) anode/borane derivative layer/electron injection layer/cathode;
(4) anode/hole injection layer/borane derivative layer/electron injection layer/cathode;
(5) anode/hole injection layer/borane derivative layer/electron transport layer/interlayer/cathode;
(6) anode/hole injection layer/hole transport layer/borane derivative layer/electron injection layer/cathode; and
(7) anode/hole injection layer/hole transport layer/borane derivative layer/electron injection layer/interlayer/cathode.

Although hole injection layers, electron injection layers, hole transport layers, electron transport layers and interlayers are not always essential in this invention, they improve the luminous efficiency. Particularly, the hole injection layer and the hole transport layer significantly improve the luminous efficiency.

The organic EL device according to this invention is preferably supported on the substrate. Any substrate may be used as far as it has sufficient mechanical strength, thermal stability and transparency. Glass and transparent plastic film, etc. may be cited as examples.

Anode materials used for the anode of the organic EL device of this invention include metals, metal alloys, electrically conductive compounds and mixtures thereof, which have a work function of more than 4 eV. Metals such as Au and electroconductive transparent materials such as CuI, indium tin oxide (hereinafter referred to as "ITO"), $SnO_2$ and ZnO may be cited as examples.

Cathode materials used for the cathode of the organic EL device of this invention include metals, metal alloys, electrically conductive compounds and mixtures thereof, which have a work function of less than 4 eV. Calcium, magnesium, lithium, aluminum, magnesium alloy, lithium alloy, aluminum alloy, and mixtures of aluminum/lithium, magnesium/silver and magnesium/indium, etc. may be cited as examples.

In this invention, the light transmittance of at least one electrode is preferably not less than 10% so as to efficiently obtain the light emission from the organic EL device. The sheet resistance as an electrode is preferably not more than several hundred Ω/mm. The film thickness depends on the property of electrode materials, but it is usually selected within a range of 10 nm to 1 μm, and preferably 10–400 nm. Such electrodes may be manufactured by a method such as vapor deposition and sputtering wherein a thin film is formed using the above-mentioned electrode material (anode material and cathode material).

The luminescent layer as an essential layer of the organic EL device of this invention preferably comprises the borane derivatives represented by the aforementioned formula (2). However, any luminescent materials other than the borane derivatives of this invention may be used. It is also possible to use the mixture of the borane derivatives of the formula (2) and other luminescent material in order to obtain a light wavelength different from that of the borane derivative, or to enhance the luminous efficiency. Further, there is no problem in using two or more borane derivatives of the formula (2) in combination.

The luminescent materials other than the borane derivatives of the formula (2) may include various known materials such as daylight fluorescent materials mentioned in "Optical Function Materials", Functional Polymer Material Series, Society of Polymer Science, Japan ed., Kyoritsu Shuppan Co., Ltd. (1991), p. 236, optical whitening agents, laser dyes, organic scintillators, various fluorescence analysis reagents.

Specifically, preferred are polycyclic condensation compounds such as anthracene, phenanthrene, pyrene, chrysene, perylene, coronene, rubrene and quinacridone; oligophenylene compounds such as quarterphenyl; scintillators for the liquid scintillation such as 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-tert-butyl-2-benzoxazolyl)thiophene, 1,4-diphenyl-1,3-butadiene, 1,6-diphenyl-1,3,5-hexatriene and 1,1,4,4-tetraphenyl-1,3-butadiene; metal complexes of oxine derivatives disclosed in JP-A 63-264692; coumarin dyes; dicyanomethylene pyran dyes; dicyanomethylene thiopyran dyes; polymethine dyes; oxobenzanthracene dyes; xanthene dyes; carbostyril dyes and perylene dyes; oxazine compounds disclosed in Germany Patent No. 2534713; stilbene derivatives disclosed in the 40th Japan Applied Physics Related Association Lecture Proc., 1146 (1993); spiro compounds disclosed in JP-A 7-278537; and oxadiazoles disclosed in JP-A 4-363891.

The hole injection layer, which is an optional layer of the organic EL device of this invention, can be prepared by using the hole injection material. The hole injection layer may be prepared as a single layer comprising one or more hole injection materials or as multiple hole injection layers comprising various hole injection materials.

The hole transport layer, which is an optional layer of the organic EL device of this invention, can be prepared by using the hole transport material. The hole transport layer may be prepared as a single layer comprising one or more hole transport materials or as multiple hole transport layers comprising various hole transport materials.

The hole injection material and the hole transport material may comprise the borane derivatives of the formula (2), but it is also possible to use any material which has been conventionally used as a charge transport material for an positive hole in a photoconductive material, or any known material which can be used for hole injection layers or hole transport layers of the organic EL devices.

Concrete examples of such known materials include, for example, carbazole derivatives (e.g., N-phenyl carbazole, polyvinyl carbazole, etc.); triarylamine derivatives (e.g., TPD, polymers having an aromatic tertiary amine in its principal chain or its side-chain, 1,1-bis(4-di-p-tolylaminophenyl)cyclohexane, N,N'-diphenyl-N,N'-dinaphthyl-4,4'-diaminobiphenyl (hereinafter abbreviated as "NPD"), 4,4',4"-tris{N-(3-methylphenyl)-N-phenylamino}-triphenylamine, compounds disclosed in Journal of the Chemical Society, Chemical Communication, p. 2175 (1996), compounds disclosed in JP-A 57-144558, JP-A 61-62038, JP-A 61-124949, JP-A 61-134354, JP-A 61-134355, JP-A 61-112164, JP-A 4-308688, JP-A 6-312979, JP-A 6-267658, JP-A 7-90256, JP-A 7-97355, JP-A 6-1972, JP-A 7-126226, JP-A 7-126615, JP-A 7-331238, JP-A 8-100172 and JP-A 8-48656, and star-burst amine derivatives described in Advanced Material, Vol. 6, p. 677 (1994), etc.), stilbene derivatives (those disclosed in 72nd CSJ (the Chemical Society of Japan) National Meeting, Lecture Proc. (II), p. 1392, 2PB098, etc.); phthalocyanine derivatives (non-metal, copper phthalocyanine, etc.); and polysilanes.

The electron injection layer, which is an optional layer of the organic EL device of this invention, can be prepared by using the electron injection material. The electron injection layer may be prepared as a single layer comprising one or more electron injection materials or as a multiple electron injection layer comprising various electron injection materials.

The electron transport layer, which is an optional layer of the organic EL device of this invention, can be prepared by using the electron transport material. The electron transport layer may be prepared as a single layer comprising one or more electron transport materials or as a multiple electron transport layer comprising various electron transport materials.

The electron injection material and the electron transport material preferably comprise the borane derivatives of the formula (2), but it is also possible to use any material which has been conventionally used as an electron transfer compound in a photoconductive material, or any known material which can be used for electron injection layers or electron transport layers of the organic EL devices.

Concrete examples of such known materials include, for example, diphenylquinone derivatives (those disclosed in Journal of the Society of Electrophotography of Japan, 30, 3 (1991), etc.), perylene derivatives (those described in J. Apply. Phys., 27, 269 (1988), etc.), oxadiazole derivatives (those disclosed in the above mentioned Lit., Jpn. J. Appl. Phys., 27, L713 (1988), and Appl. Phys. Lett., 55, 1489 (1989), etc.), thiophene derivatives (those disclosed in JP-A 4-212286, etc.), triazole derivatives (those disclosed in Jpn. J. Appl. Phys., 32, L917 (1993), etc.), thiadiazole derivatives (those disclosed in Polymer Preprints, Japan, Vol. 43, No. 3 (1994), (III) Pla007, etc.), metal complexes of oxine derivatives (those disclosed in Technical Report of Institute of Electronics, Information and Communication Engineers, 92 (311), 43 (1992), etc.), polymers of quinoxaline derivatives (those disclosed in Jpn. J. Appl. Phys., 33, L250 (1994), etc.), and phenanthroline derivatives (those disclosed in Polymer Preprints, Japan, Vol. 43, No. 7 (1994), 14J07, etc.)

Hole injection materials, hole transport materials, luminescent materials and electron injection materials, which are usable in the organic EL device of this invention, preferably have a Tg of not less than 80° C., more preferably not less than 100° C.

Preferable interlayers, which are optional layers of the organic EL device of this invention, are those which can promote the injection of the electron from the cathode, and those which can prevent the positive hole from flowing into the cathode. These are selected according to the compatibility with the material used for the cathode. Lithium fluoride, magnesium fluoride, calcium fluoride, etc. may be cited as concrete examples.

Each layer constituting the organic EL device of this invention may be prepared by forming the material for constituting the layer into a thin film by any known method such as vapor deposition, spin coating and casting.

The film thickness of each layer formed by such a method is not particularly limited, and it can be properly determined depending upon properties of the material used. It is usually selected within the range of 2 nm to 5000 nm.

When the vapor deposition method is used to form the material into a thin film, the depositing conditions may be varied depending on the kind of the borane derivatives, the crystalline structure and the associated structure of the intended molecular built-up film. In general, it is preferably selected within the following ranges: the boat heating temperature of 50 to 400° C., vacuum of $10^{-6}$ to $10^{-3}$ Pa, deposition rate of 0.01 to 50 nm/sec., substrate temperature of −150 to +300° C., and film thickness of 5 nm to 5 µm.

Next, the method of manufacturing the organic EL device, which has the aforementioned structure (1) comprising anode/borane derivative layer/cathode, is explained as an example of the method for producing the organic EL device of this invention.

A thin film comprising an anode material is formed on an adequate substrate by the vapor deposition method so as to be 1 µm or less, preferably 10 to 200 nm, in thickness. Then, a thin film of the borane derivative is formed onto the resulting anode layer to obtain a luminescent layer. A thin film comprising a cathode material is formed onto the luminescent layer by the vapor deposition method so as to be 1 µm or less in thickness, resulting in a cathode layer. The desired organic EL device is thus obtained.

Alternatively, the order of manufacturing the above-mentioned organic EL device can be reversed, namely, the cathode, the luminescent layer and the anode may be produced in order.

When applying a DC voltage to the resultant organic EL device, it may be applied with the anode set to a positive polarity and the cathode set to a negative polarity. If applying a voltage of approximately 2 to 40 V, the light emission can be observed from the transparent or semi-transparent electrode side (anode or cathode, and both).

This organic EL device can emit lights as well when applying an AC voltage. Any waveform of the AC may be applied.

BEST MODE FOR CARRYING OUT THE INVENTION

Now, the present invention shall specifically be explained with reference to the following examples, but this invention shall not be limited thereto.
Synthesis of Borane Derivatives

EXAMPLE 1

Synthesis of the Compound of the Formula (4)

13 ml of a hexane solution of n-butyl lithium (1.6 mol/l) was added to 30 ml of an ethereal solution containing 5.14 g of 9-bromoanthracene at −78° C. under argon flow. The temperature was then raised to 0° C. and the reaction mixture was stirred for 30 minutes. Subsequently, the mixture was added to 10 ml of an ethereal solution containing 4.1 ml of boron trifluoride at that temperature and the solution was stirred for 1 hour to yield a precipitate as a yellow solid.

The supernatant was then removed and 30 ml of dry ether was added to the precipitate. After stirring for 1 hour, the supernatant was again removed and 30 ml of dry THF was added.

Further, an ethereal solution of 9,10-dilithioanthracene was added dropwise to the solution, which was stirred for 3 hours at room temperature. Precipitates were removed by filtration and the filtrate was concentrated. Ethyl acetate was added to the concentrate and the precipitate was recrystallized from ethyl acetate to yield the desired compound (4% yield). This compound emitted red fluorescence in a solid state.

$^1$H-NMR ($C_6D_6$): δ=6.41 (dd, 4H), 6.77 (t, 8H), 7.06 (t, 8H), 7.77 (d, 8H), 8.35 (s, 4H), and 8.59–8.63 (m, 12H).

EXAMPLE 2

Synthesis of the Compound of the Formula (6)

The title compound was synthesized according to the method as described in Example 1, except that 9,10-dilithioanthracene was replaced by mesityl lithium.

$^1$H-NMR ($C_6D_6$): δ=2.0 (s, 6H), 2.10 (s, 3H), 6.71 (s, 2H), 6.91 (t, 4H), 6.88–6.94 (m, 4H), 7.06–7.12 (m, 4H), 8.35 (s, 2H), and 8.49 (d, 4H).

EXAMPLE 3

Synthesis of the Compound of the Formula (3)

13 ml of a hexane solution of n-butyl lithium (1.6 mol/l) was added to 30 ml of an ethereal solution containing 5.14 g of 9-bromoanthracene at −78° C. under argon flow. The temperature was then raised to 0° C. and the reaction mixture was stirred for 30 minutes. Subsequently, the mixture was added to 10 ml of an ethereal solution containing 0.8 ml of boron trifluoride at that temperature and the solution was stirred for 12 hour to give a precipitate as an orange solid.

The precipitate was recrystallized from benzene to yield the desired compound (33% yield).

$^1$H-NMR (C$_6$D$_6$): δ=6.83–6.89 (m, 6H), 7.21 (t, 4H), 7.95 (d, 6H), 8.12 (d, 6H), and 8.58 (s, 4H).

Preparation of Organic EL Devices and Properties Thereof

EXAMPLE 4

ITO was deposited in a thickness of 100 nm on a glass substrate (25 mm×75 mm×1.1 mm) (manufactured by Tokyo Sanyo Vacuum Co., Ltd.) by a vapor deposition method, which was used as a transparent support substrate. This transparent support substrate was fixed in a substrate holder of a commercially available vapor deposition apparatus (manufactured by Sinku Kiko Co., Ltd.), which was equipped with a quartz crucible containing N,N'-dinaphtyl-N,N'-diphenylbenzidine (hereafter abbreviated as "NPD"), a quartz crucible containing the compound of the formula (10), a quartz crucible containing 1,1-dimethyl-2,5-bis{2-(2-pyridyl)pyridyl}-3,4-diphenylsilacyclopentadiene (hereafter abbreviated as "PYPY"), a graphite crucible containing magnesium and a graphite crucible containing silver.

The vacuum chamber was evacuated to 1×10$^{-3}$ Pa, and then the crucible containing NPD was heated so that NPD could be vapor-deposited to have a film thickness of 50 nm, thus forming a positive hole transport layer. Next the crucible containing the compound of the formula (10) was heated so that the compound could be vapor-deposited to have a film thickness of 15 nm, thus forming a luminescent layer. Further, the crucible containing PYPY was heated so that PYPY could be vapor-deposited to have a film thickness of 35 nm, thus forming an electron transport layer. The rate of vapor deposition was each 0.1 to 0.2 nm/sec.

Subsequently, the vacuum chamber was evacuated to 2×10$^{-4}$ Pa, and then the graphite crucibles were heated to deposit magnesium at a deposition rate of 1.2 to 2.4 nm/sec, and simultaneously, to deposit silver at a deposition rate of 0.1 to 0.2 nm/sec. A 150-nm alloy electrode of magnesium and silver was formed on the organic layer, whereby an organic EL device was obtained.

The ITO electrode was used as an anode and the alloy electrode of magnesium and silver as a cathode. When a DC voltage was applied thereto, a current of about 1 mA/cm$^2$ flowed and green light having a brightness of about 100 cd/m$^2$ and a wavelength of 515 nm was emitted.

COMPARATIVE EXAMPLE 1

A device was prepared according to the method as described in Example 4, except that the compound of the formula (10) was replaced by tris(8-hydroxyquinoline)-aluminum.

The ITO electrode was used as the anode and the alloy electrode of magnesium and silver as the cathode. When a DC voltage was applied thereto, a current of about 1 mA/cm$^2$ flowed and green light having a brightness of about 20 cd/m$^2$ and a wavelength of 522 nm was emitted. The emission brightness was lowered to about one-fifth as compared with that obtained in Example 4.

COMPARATIVE EXAMPLE 2

A device was prepared according to the method as described in Example 4, except that the compound of the formula (10) was replaced by trimesityl borane.

The ITO electrode was used as the anode and the alloy electrode of magnesium and silver as the cathode. When a DC voltage was applied thereto, a current of about 50 mA/cm$^2$ flowed and purple light having a brightness of about 5 cd/m$^2$ was emitted. The emission brightness and the emission efficiency were lowered to a great extent as compared with those obtained in Example 4.

EXAMPLE 5

A device was prepared according to the method as described in Example 4, except that PYPY was not used and that the thickness of the layer comprising the compound of the formula (10) was changed to 50 nm.

The ITO electrode was used as the anode and the alloy electrode of magnesium and silver as the cathode. When a DC voltage was applied thereto, a current of about 1 mA/cm$^2$ flowed and green light having a brightness of about 6 cd/m$^2$ and a wavelength of 515 nm was emitted.

EXAMPLE 6

A device was prepared according to the method as described in Example 4, except that the compound of the formula (10) was replaced by the compound of the formula (4).

The ITO electrode was used as the anode and the alloy electrode made of magnesium and silver as the cathode. When a DC voltage was applied thereto, a current of about 1 mA/cm$^2$ flowed and red light having a brightness of about 6 cd/m$^2$ and a wavelength of 616 nm was emitted.

EXAMPLE 7

A device was prepared according to the method as described in Example 4, except that the compound of the formula (10) was replaced by the compound of the formula (11).

The ITO electrode was used as the anode and the alloy electrode of magnesium and silver as the cathode. When a DC voltage was applied thereto, a current of about 1 mA/cm$^2$ flowed and blue light having a brightness of about 30 cd/m$^2$ and a wavelength of 464 nm was emitted.

EXAMPLE 8

The transparent support substrate used in Example 4 was fixed in the substrate holder of the vapor deposition apparatus, which was equipped with a quartz crucible containing NPD, a quartz crucible containing the compound of the formula (10), a tungsten crucible containing aluminum and a tungsten crucible containing lithium fluoride.

The vacuum chamber was evacuated to 1×10$^{-3}$ Pa, and then the crucible containing NPD was heated so that NPD could be vapor-deposited to have a film thickness of 50 nm, thus forming a positive hole transport layer. Next the crucible containing the compound of the formula (10) was heated so that the compound could be vapor-deposited to have a film thickness of 50 nm, thus forming an electron-transporting luminescent layer. The rate of vapor deposition was each 0.1 to 0.2 nm/sec.

Subsequently, the vacuum chamber was evacuated to 2×10$^{-4}$ Pa, and then the tungsten crucibles were heated so that lithium fluoride could be vapor-deposited to have a film thickness of 2 nm on the organic layer and finally aluminum could be vapor-deposited to have a film thickness of 100 nm on the organic layer, whereby an organic EL device was obtained.

The ITO electrode was used as the anode and the alloy electrode of magnesium and silver as the cathode. When a DC voltage was applied thereto, a current of about 2 mA/cm² flowed and green light having a brightness of about 100 cd/m² and a wavelength of 515 nm was emitted.

EXAMPLE 9

A device was prepared according to the method as described in Example 8, except that the compound of the formula (10) was replaced by the compound of the formula (4).

The ITO electrode was used as the anode and the alloy electrode of magnesium and silver as the cathode. When a DC voltage was applied thereto, a current of about 2 mA/cm² flowed and red light having a brightness of about 15 cd/m² and a wavelength of 616 nm was emitted.

EXAMPLE 10

A device was prepared according to the method as described in Example 4, except that the compound of the formula (10) was replaced by the compound of the formula (9).

The ITO electrode was used as the anode and the alloy electrode of magnesium and silver as the cathode. When a DC voltage was applied thereto, a current of about 2 mA/cm² flowed and blue light having a brightness of about 100 cd/m² and a wavelength of 477 nm was emitted.

EXAMPLE 11

A device was prepared according to the method as described in Example 4, except that the compound of the formula (10) was replaced by the compound of the formula (12).

The ITO electrode was used as the anode and the alloy electrode of magnesium and silver as the cathode. When a DC voltage was applied thereto, a current of about 0.7 mA/cm² flowed and green light having a brightness of about 100 cd/m² and a wavelength of 511 nm was emitted.

EXAMPLE 12

A device was prepared according to the method as described in Example 4, except that the compound of the formula (10) was replaced by the compound of the formula (13).

The ITO electrode was used as the anode and the alloy electrode of magnesium and silver as the cathode. When a DC voltage was applied thereto, a current of about 30 mA/cm² flowed and red light having a brightness of about 100 cd/m² and a wavelength of 622 nm was emitted.

EXAMPLE 13

The transparent support substrate used in Example 4 was fixed in the substrate holder of the vapor deposition apparatus, which was equipped with a quartz crucible containing NPD, a quartz crucible containing the compound of the formula (10), a quartz crucible containing the compound of the formula (11), a quartz crucible containing PYPY, a tungsten crucible containing aluminum and a tungsten crucible containing lithium fluoride.

The vacuum chamber was evacuated to $1\times10^{-3}$ Pa, and then the crucible containing NPD was heated so that NPD could be vapor-deposited to have a film thickness of 50 nm, thus forming a positive hole transport layer. Next the crucible containing the compound of the formula (10) and the crucible containing the compound of the formula (11) were heated so that the compounds could be vapor-deposited to have a film thickness of 15 nm, thus forming a luminescent layer. Further, the crucible containing PYPY was heated so that PYPY could be vapor-deposited to have a film thickness of 35 nm, thus forming an electron transport layer. In this process, the composition ratio of the respective compounds was 2% of the compound of the formula (10) to 98% of the compound of the formula (11).

Subsequently, the vacuum chamber was evacuated to $2\times10^{-4}$ Pa, and then the tungsten crucibles were heated so that lithium fluoride could be vapor-deposited to have a film thickness of 0.5 nm on the organic layer and aluminum could finally be vapor-deposited to have a film thickness of 100 nm on the organic layer, whereby an organic EL device was obtained.

The ITO electrode was used as the anode and the alloy electrode of magnesium and silver as the cathode. When a DC voltage was applied thereto, a current of about 1 MA/cm² flowed and bluish green light having a brightness of about 100 cd/m² and a wavelength of 495 nm was emitted.

EXAMPLE 14

A device was prepared according to the method as described in Example 13, except that the compound of the formula (10) was replaced by the compound of the formula (14) and that the compound of the formula (11) was replaced by tris(8-hydroxyquinoline)aluminum.

The ITO electrode was used as the anode and the alloy electrode of magnesium and silver as the cathode. When a DC voltage was applied thereto, a current of about 20 mA/cm² flowed and red light having a brightness of about 100 cd/m² and a wavelength of 600 nm was emitted.

INDUSTRIAL APPLICABILITY

The borane derivative, the new compound of the present invention has a high luminescence efficiency in a solid state and is therefore suitable for a luminescent material. It is also useful for electrophotography and as photoelectronic functional materials such as nonlinear optical materials and conductive materials.

Further, the organic EL device of the present invention contains a luminescent material having a high luminescent efficiency, and therefore, it can provide a display having a low power consumption and a long life.

What is claimed is:

1. An organic electroluminescent device comprising a borane derivative represented by the following formula (2):

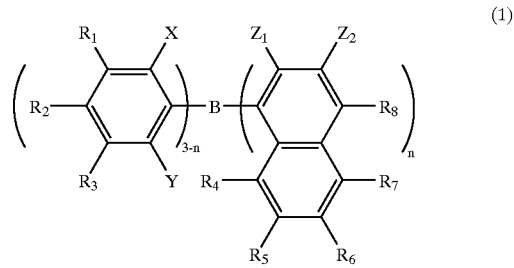

(1)

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3;

further wherein when n is two or more, $Z_1$s may be different from each other.

2. The organic electroluminescent device according to claim 1, having a luminescent layer which comprises one borane derivative represented by the formula (2) or a mixture of two or more borane derivatives represented by the formula (2), or a mixture of at least one borane derivative represented by the formula (2) and at least one luminescent material other than the borane derivatives represented by the formula (2).

3. The organic electroluminescent device according to claim 1, having a charge transport layer which comprises the borane derivative represented by the formula (2).

4. The organic electroluminescent device according to claim 1, wherein the borane derivative is a compound wherein at least one substituted or unsubstituted 9-anthryl group is bonded to the boron atom.

5. The organic electroluminescent device according to claim 2, wherein the borane derivative is a compound wherein at least one substituted or unsubstituted 9-anthryl group is bonded to the boron atom.

6. The organic electroluminescent device according to claim 3, wherein the borane derivative is a compound wherein at least one substituted or unsubstituted 9-anthryl group is bonded to the boron atom.

7. An organic electroluminescent device comprising at least an anode, a cathode and a luminescent layer interposed therebetween, the luminescent layer comprising a borane derivative represented by the following formula (2):

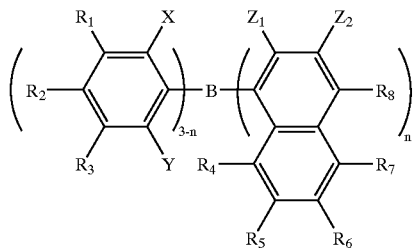

(2)

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3, further wherein when n is two or more, $Z_1$s may be different from each other.

8. The organic electroluminescent device according to claim 7, wherein the borane derivative is a compound wherein at least one substituted or unsubstituted 9-anthryl group is bonded to the boron atom.

9. The organic electroluminescent device according to claim 7, further comprising a charge transfer layer.

10. The organic electroluminescent device according to claim 9, wherein the charge transfer layer comprises a borane derivative represented by the following formula (2):

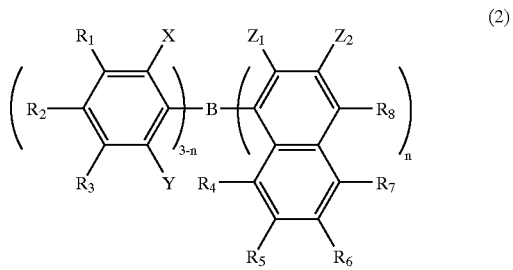

(2)

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3, further wherein when n is two or more, $Z_1$s may be different from each other.

11. A method of producing electroluminescence comprising providing a luminescent material and applying voltage across the luminescent material so that the luminescent material can exhibit electroluminescence, wherein the luminescent material comprises a borane derivative represented by the following formula (2):

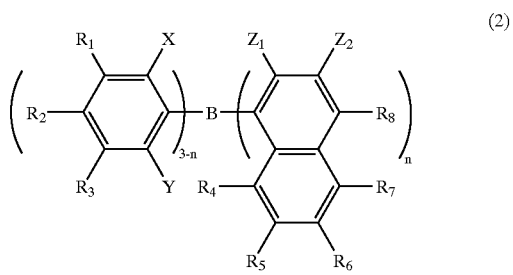

(2)

wherein $R_1$ to $R_8$ and $Z_2$ are each independently a hydrogen atom, a saturated or unsaturated hydrocarbon group, an aromatic group, a heterocyclic group, a substituted amino group, a substituted boryl group, an alkoxy group or an aryloxy group; X, Y and $Z_1$ are each independently a saturated or unsaturated hydrocarbon group, an aromatic group, a heterocyclic group, a substituted amino group, an alkoxy group or an aryloxy group; substituents of $Z_1$ and $Z_2$ may be united to form a condensed ring; and n is an integer of 1–3;

further wherein when n is two or more, $Z_1$s may be different from each other.

* * * * *